(12) United States Patent
Kitagawa et al.

(10) Patent No.: US 7,449,890 B2
(45) Date of Patent: Nov. 11, 2008

(54) APPARATUS AND METHOD FOR CIRCULATED FLOW NUCLEAR MAGNETIC RESONANCE MEASUREMENT

(75) Inventors: Isao Kitagawa, Kokubunji (JP); Michiya Okada, Mito (JP)

(73) Assignee: Hitachi, Ltd., Tokyo (JP)

( * ) Notice: Subject to any disclaimer, the term of this patent is extended or adjusted under 35 U.S.C. 154(b) by 65 days.

(21) Appl. No.: 11/798,015

(22) Filed: May 9, 2007

(65) Prior Publication Data

US 2007/0273381 A1 Nov. 29, 2007

(30) Foreign Application Priority Data

May 24, 2006 (JP) ............................. 2006-143474

(51) Int. Cl.
*G01V 3/00* (2006.01)
(52) U.S. Cl. ...................................... 324/321; 324/318
(58) Field of Classification Search ......... 324/300–324; 600/407–422
See application file for complete search history.

(56) References Cited

U.S. PATENT DOCUMENTS 6,319,894 B1 * 11/2001 Tracey et al. .................. 514/8
7,157,699 B2 * 1/2007 Ouyang et al. ............... 250/281

FOREIGN PATENT DOCUMENTS

WO   WO 01/23889 A1   9/2000
WO   WO 03/007009 A2   1/2003

* cited by examiner

*Primary Examiner*—Brij B Shrivastav
(74) *Attorney, Agent, or Firm*—Reed Smith LLP; Stanley P. Fisher, Esq.; Juan Carlos A. Marquez, Esq.

(57) ABSTRACT

Briefly, the present invention provides an apparatus and a method for performing a nuclear magnetic resonance (NMR) measurement on a sample solution containing small molecules and large molecules such as proteins, and provides an apparatus and a method for repeatedly performing the NMR measurement while stably controlling concentration conditions in a sample and changing a concentration of small molecules.

A sample solution containing small molecules and large molecules is circularly transferred between a vessel equipped with a nuclear magnetic resonance probe and a control section in which injection and filtration of small molecules are performed. By transferring the sample solution between them, the NMR measurement can be performed while maintaining a concentration of large molecules to be constant and increasing or reducing a concentration of small molecules so that a concentration ratio of the small molecules relative to the large molecules is changed, the two types of molecules being present in the sample solution.

10 Claims, 11 Drawing Sheets

FIG.5A
FIG.5B
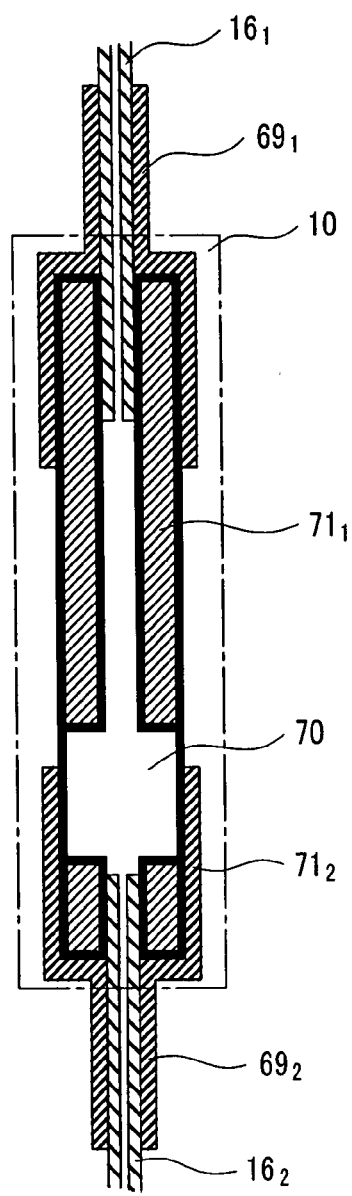
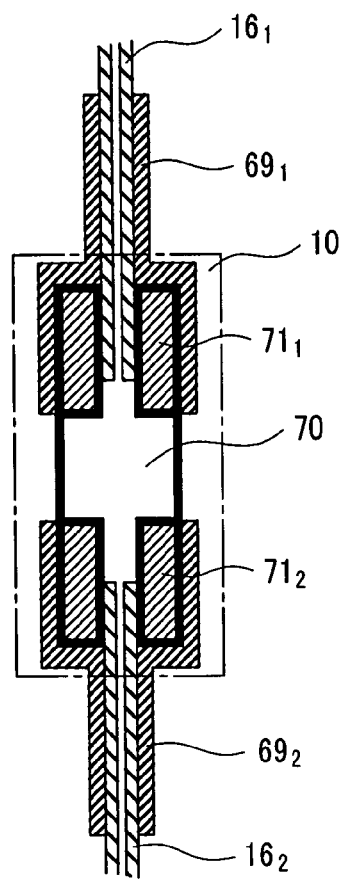

APPARATUS AND METHOD FOR CIRCULATED FLOW NUCLEAR MAGNETIC RESONANCE MEASUREMENT

CLAIM OF PRIORITY

The present invention claims priority from Japanese application JP 2006-143474 filed on May 24, 2006, the content of which is hereby incorporated by reference on to this application.

BACKGROUND OF THE INVENTION

1. Field of the Invention

The present invention relates to an apparatus and a method for repeatedly performing a nuclear magnetic resonance measurement on a sample while changing measurement conditions.

2. Description of the Related Art

Molecules with functional properties in a living body, such as proteins, have larger molecular weight than compounds used for medicine and include properties of large molecules.

Large molecules representing proteins have a molecular function in a solution. The molecular function may be impaired or promoted by combining with specific small molecules.

Binding of and interaction of a specific small molecule with a specific large molecule have been detected by use of various methods. Especially, a measurement using nuclear magnetic resonance (hereinafter referred to as an NMR measurement) allows information on the structure of a large molecule or information on the structure of a small molecule to be directly observed. In addition, such an NMR measurement allows for evaluation of dissociation constants of and reaction rates of a large molecule and a small molecule based on changes in spectrum to be measured for a molecule concentration and allows for analysis of interaction of a large molecule with a small molecule based on the structures of the large molecule and small molecule. International Publication Number WO 01/23889 discloses a method for performing an NMR measurement on the interaction of a protein with a small molecule.

Among large molecules used for an NMR measurement, a protein is produced by the following methods: a method for extracting from a living organism present in nature; a method for extracting from a large-scale expression system using *Escherichia coli*, etc. containing genes relating to production of a protein; a method using a cell-free expression system having the ability to abundantly express proteins without using a living cell; or the like. A method for radiolabeling (hereinafter referred to as labeling) with isotopes of hydrogen, carbon, and nitrogen, which are main elements of a protein, is used in some cases. The labeling includes a method for labeling by combining three elements of hydrogen, carbon, and nitrogen (which are main elements of a protein), a method for labeling all elements, and a method for selective labeling to label only atoms belonging to a specific amino acid residue, and the like. Irrespective of the type of the methods, the cost for the labeling process is high.

A nuclear magnetic resonance spectroscopy apparatus (hereinafter referred to as an NMR apparatus) typically includes a magnet for generating a static magnetic field $B_0$ and a nuclear magnetic resonance probe arranged in a bore of the magnet. The nuclear magnetic resonance probe includes one or more coils used to apply a radio frequency magnetic field $B_1$ to a target sample and detect a reaction (response) of the sample to the magnetic field.

Conventional nuclear magnetic resonance probes include a probe for measuring a stationary sample and a flow through probe. For the probe for measuring a stationary sample, a sample is placed in a glass tube or ampoule (hereinafter referred to as a sample tube), and the sample tube is set at a predetermined position in an NMR apparatus so as to perform a measurement of the sample.

In a conventional probe for measuring a stationary sample, an NMR measurement is performed while small molecules are titrated by using a sample tube having an opening, which allows for detection of changes in NMR spectrum in response to an increase in molecule concentration. However, a sample solution includes large molecules, small molecules for evaluation of an effect as an agent, and another reagent. Thus, once the sample solution contains small molecules with a certain molecule concentration, it is difficult to perform an NMR measurement with the sample solution containing small molecules with a molecule concentration smaller than the certain molecule concentration. The concentration of small molecules is, in general, measured as a parameter while the amount of large molecules in a sample solution of a predetermined amount is maintained to be constant. If a buffer solution is injected to reduce the concentration of the small molecules, the amount of the sample solution is increased. Reducing the amount of the sample solution to a predetermined amount also reduces the amount of the large molecules, resulting in a change in the measurement condition.

Titration of small molecules in a sample tube used in the NMR measurement increases the entire volume of a sample solution, which causes a change in the concentration of large molecules present in the sample solution and a change in the solution level of the sample solution. In order to reduce the changes, it is necessary that the volume of a solution to be dropped be as small as possible compared with the volume of the sample solution.

To reduce the volume of the solution to be dropped, it is necessary that the concentration of small molecules be increased. The maximum concentration of small molecules in a solution to be dropped, however, is determined based on the solubility of the small molecules. In general, the solubility of a substance varies depending on the type of a solvent and the temperature of a solution. Therefore, in an NMR measurement with a change in the concentration of small molecules due to the drop, the type of the solvent and the temperature of the solution influence stability of the concentration of large molecules.

On the other hand, International Publication Number WO 03/007009 discloses a flow through probe including a sample inlet port, a sample outlet port, and an internal tube extending between the sample inlet port and the sample outlet port. The internal tube includes a cell for holding a sample. A sample is placed into the sample inlet port, flows through the internal tube, and enters the cell. After being measured, the sample flows through the internal tube and is taken out of the probe.

A conventional flow through probe is used in combination with a robot type sample transfer system. Flow through probes each combined with a different sample transfer system are available in the market, for example, from Gilson, Inc. For such a system, samples which are each adjusted for different measurement conditions must be prepared in a plurality of vessels. The samples are passed through an apparatus in which the samples can be taken out of the vessels and are transferred to a flow through probe which has been already set. After the NMR measurement is completed on a sample, the sample is taken out of the probe.

A combination of a conventional flow through probe with a sample transfer system requires that samples adjusted for a plurality of different concentration conditions be prepared. Thus, the number of types of solutions containing large molecules with a certain concentration is required for the number of the types of measurement conditions. This increases the cost required for the samples.

In the case of unknown large molecules or unknown small molecules, the entire measurement needs to be repeated to evaluate functional properties of the molecules until a desired range of measurement conditions and a desired degree of changes in measurement conditions are confirmed.

SUMMARY OF THE INVENTION

The present invention provides an apparatus and a method for a nuclear magnetic resonance measurement on a sample solution containing small molecules and large molecules such as proteins and provides an apparatus and a method for repeatedly performing a nuclear magnetic resonance measurement while controlling concentration conditions in a sample and changing a concentration of small molecules.

According to the present invention, a sample vessel equipped with a nuclear magnetic resonance probe is coupled to sample tubing (which includes sample transfer tubes). The sample vessel and the sample tubing form a closed loop. A liquid transfer pump is provided in the closed loop so that a liquid can be circularly transferred in the closed loop. A part of the sample tubing is provided with a control section having means for introducing large molecules (sample), small molecules (which are to be mixed with the large molecules), and a buffer solution so as to control sample components. Furthermore, the control section includes means for selectively discharging the small molecules or the buffer solution in the case where the amount of a solution injected exceeds the entire volume of the closed loop, and controls sample components. The present invention allows for an NMR measurement in which a concentration of small molecules is increased or decreased so that a concentration ratio of the small molecules relative to the large molecules is changed while maintaining the amount of the large molecules to a predetermined value (maintaining a concentration of the large molecules to a constant level), the two types of molecules being present in a sample solution.

According to the present invention, a method for the NMR measurement on a solution containing large molecules and small molecules comprises the step of increasing or reducing a concentration of the small molecules while maintaining a concentration of the large molecules to a constant level, which makes it possible to measure a change in NMR spectrum while controlling the concentration ratio of the small molecules relative to the large molecules and maintaining the amount of the large molecules to a constant value.

According to the present invention, in a method for the NMR measurement on a solution containing large molecules and small molecules, the volume of a solution in a NMR measurement vessel does not change due to a drop of a solution. Therefore, the NMR measurement can be performed while maintaining the concentration of the large molecules present in the NMR measurement vessel to a constant level irrespective of the temperature of a sample solution and solubility of the small molecules.

BRIEF DESCRIPTION OF THE DRAWINGS

FIGS. 5A and 5B are diagrams showing two examples of another type of connections of the vessel 10 with the sample transfer tubes $16_1$ and $16_2$.

DETAILED DESCRIPTION OF THE PREFERRED EMBODIMENTS

A description will be made of preferred embodiments of the configuration of an apparatus for a circulated flow NMR measurement and preferred embodiments of a method for the circulated flow NMR measurement on a sample solution according to the present invention with reference to the accompanying drawings.

First Embodiment

Figure 1:
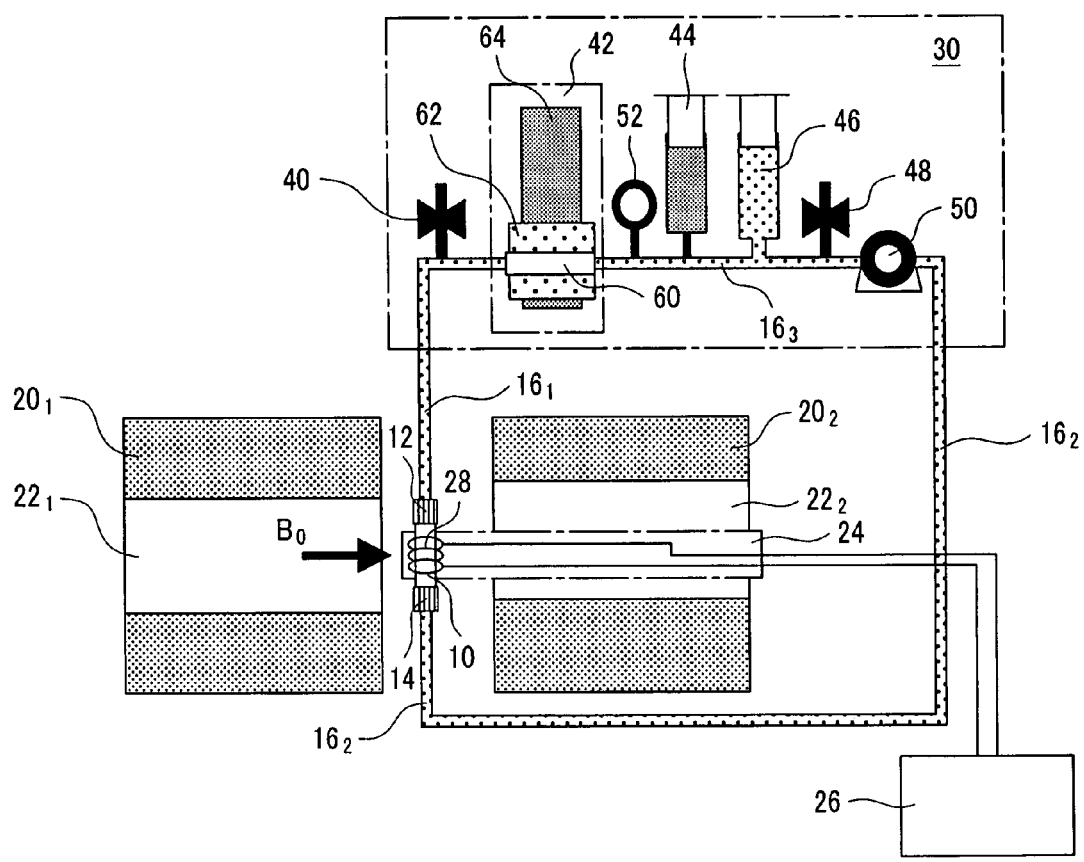
FIG. 1 is a diagram showing the concept of a circulated flow nuclear magnetic resonance measurement apparatus for measuring a sample solution according to a first embodiment of the present invention.

FIG. 1 is a diagram showing the concept of an apparatus for a circulated flow nuclear magnetic resonance measurement on a sample solution according to a first embodiment of the present invention. Reference numerals $20_1$ and $20_2$ denote separated magnets for applying a magnetic field to a sample. The separated magnets $20_1$ and $20_2$ have bores $22_1$ and $22_2$, respectively. Reference numeral 24 denotes a nuclear magnetic resonance probe, which is held in the bore $22_2$. The nuclear magnetic resonance probe 24 is provided with a vessel 10 for storing a constant amount of a sample. The vessel 10 is positioned in an area of a magnetic field generated by the separated magnets $20_1$ and $20_2$. In general, the vessel 10 is preferably made of silica glass. A detection coil 28 used to detect a nuclear magnetic resonance signal is disposed with an optimal positional relationship with the vessel 10. A transmission coil is provided to excite a sample with a predetermined high frequency signal. The transmission coil, however, is not illustrated to avoid complication of the drawing. Sample tube connection sections 12 and 14 are provided at the upper and lower end portions of the vessel 10, respectively.

The vessel 10 is fluidically connected with sample transfer tubes $16_1$ and $16_2$ through the sample tube connection sections 12 and 14. The vessel 10, the sample transfer tubes $16_1$, $16_2$ and a sample transfer tube $16_3$ disposed in a control section 30 (which is described later) form a closed loop allowing a sample to be circulated. In the first embodiment, the vessel 10, the sample tube connection sections 12, 14, and connection portions of the sample transfer tubes $16_1$, $16_2$ are arranged on the same axis. A linear portion (which is a part of the closed loop formed by connecting the vessel 10 and the sample transfer tubes $16_1$, $16_2$, $16_3$) where the vessel 10 is coupled to the sample transfer tubes $16_1$, $16_2$ is disposed between the bore $22_1$ of the separated magnet $20_1$ and the bore $22_2$ of the separated magnet $20_2$. Reference numeral 26 denotes a transmitting/receiving system, which receives a signal from the detection coil 28 or transmits a signal to a transmission coil (not illustrated).

Reference numeral 30 is the control section provided with the sample transfer tube $16_3$, which connects the sample transfer tube $16_1$ and $16_2$. The sample transfer tube $16_3$ is coupled to: a discharge valve 40; a filter section 42; a measurement unit 52 for monitoring the state of a solution such as a pH value and pressure; a solution injection unit 44 for injecting small molecules; a sample solution injection unit 46 for injecting large molecules present in a sample; a liquid injection valve 48 for injecting a buffer solution and clean water; and a liquid transfer pump 50. With this arrangement, the vessel 10 and the sample transfer tube $16_1$, $16_2$, $16_3$ form the closed loop so that sample components can be controlled.

The type of the filter section 42 is not limited as long as the filter section 42 allows large molecules such as proteins to be separated from other components so that the large molecules and the other components are transferred to the outside of a wetted portion 60 coupled to the sample transfer tube $16_3$. It is preferred, however, that the filter section 42 use a film 62 having fine pores that do not allow proteins to pass therethrough and that allow other components including small molecules to pass therethrough. For example, a configuration obtained by combining a disk-like ultrafiltration filter manufactured by Millipore Corporation with a disk-like filter folder is preferable. With this configuration, the size of a fine pore of the disk-like ultrafiltration filter can be selectively used based on the molecular weight of proteins present in a sample solution. Thus, the ultrafiltration can be carried out on components other than proteins in a preferable manner. A liquid filtrated by the filter 62 is discharged into a liquid reservoir 64. Since large molecules are not discharged by the filter section 42, the amount of large molecules in the closed loop is maintained to be constant.

The solution injection unit 44 preferably electronically controls one or more pressure-driven syringe pumps. For example, syringe pumps IC3100 and IC3200 manufactured by KD Scientific are fluidically connected to the sample transfer tube $16_3$. With this configuration, a solution is transferred by applying pressure while a syringe which includes a solution containing small molecules is precisely controlled. Thus, a solution can be injected into the closed loop in a desired manner. When a buffer solution needs to be injected in the closed loop, the buffer solution is placed in a syringe. Then, a solution is transferred by applying pressure while the syringe is precisely controlled. Accordingly, the buffer solution can be injected into the closed loop.

Similarly to the solution injection unit 44, the sample solution injection unit 46 preferably electronically controls one or more pressure-driven syringe pumps. For example, the syringe pumps IC3100 and IC3200 manufactured by KD Scientific are fluidically connected to the sample transfer tube $16_3$. With this configuration, a solution is transferred by applying pressure while a syringe which includes a solution containing large molecules (present in a sample) is precisely controlled. Thus, a solution containing large molecules can be injected into the closed loop in a desired manner.

It is preferred that the liquid transfer pump 50 is used with High Performance Liquid Chromatography (HPLC). Preferably, a stepping motor or the like, which allows for electronic control, is used to drive a plunger so that a solution can be transferred under constant pressure in the closed loop formed by connecting the vessel 10 and the sample transfer tubes $16_1$, $16_2$, $16_3$.

The measurement unit 52 is an indicator for monitoring the state of a solution such as a pH value and pressure and can be used with HPLC.

It is necessary that materials of the sample transfer tubes $16_1$, $16_2$, $16_3$ be selected based on the properties of a sample solution. In a measurement on biological large molecules such as proteins, polyethylene ethylene ketone (PEEK), Tefzel, Kel-F, and fused silica are used in many cases. In addition, it is preferred that the inner diameter of the sample transfer tubes is 0.5 mm to 0.65 mm; the total length of the sample transfer tubes, about 4 m; and the total volume of the vessel 10 and the sample transfer tubes, about 1000 µL.

With reference to FIG. 1, the procedure for the measurement according to the first embodiment is described below.

(Injection of Buffer Solution)

First, the liquid transfer pump 50 operates while a buffer solution is supplied through the liquid injection valve 48 so as to fill the sample transfer tubes $16_1$, $16_2$, $16_3$ with the buffer solution. As a result, the vessel 10 is filled with the buffer solution and then the closed loop is filled with the buffer solution. For the buffer solution, the following are used: a buffer solution in which the ion concentration (pH value) is adjusted in order to maintain stability of large molecules such as proteins in the closed loop and to stably perform the NMR measurement; a phosphoric acid buffer solution; or the like. In the step of injecting a buffer solution, the discharge valve 40 is closed.

(Injection of Sample)

After the above step, a sample containing large molecules is placed in the sample solution injection unit 46. While the sample is controlled and a sample solution is injected, the liquid transfer pump 50 operates. It is necessary that a lock solvent required for a lock during the NMR measurement be mixed into the sample. When the majority of a solvent (such as a phosphoric acid buffer solvent which is used in a large amount during an NMR measurement on proteins) is light water, heavy water is preferably used as a lock solvent. The concentration of the heavy water is preferably 5% to 10%. Depending on large molecules to be measured, an appropriate buffer solvent and lock solvent are selected to perform the measurement. In this case, when a sample containing large molecules whose amount corresponds to the entire volume of the closed loop (formed by connecting the vessel 10, the sample transfer tube $16_1$, $16_2$, $16_3$, and the filter section 42) is injected, the buffer solution which fills the closed loop is replaced with the sample containing large molecules.

Discharge pressure of the liquid transfer pump 50 during injection of a sample solution is set to a value larger than pressure at the filter section 42 when ultrafiltration starts. An unnecessary buffer solution produced in the closed loop of the sample transfer tube $16_1$, $16_2$, $16_3$ is discharged into the liquid reservoir 64 by the filter section 42 based on the injection of the sample solution. When the volume of the solution discharged into the liquid reservoir 64 approaches to the entire volume of the closed loop formed by connecting the vessel 10, the sample transfer tube $16_1$, $16_2$, $16_3$, and the filter section 42, pressure indicated by the indicator (measurement unit 52) is reduced. Immediately after that, the discharge pressure of the liquid transfer pump 50 is set to be reduced to a level lower than pressure required for the ultrafiltration performed by use of the filter section 42. Then, the ultrafiltration performed by using the filter section 42 is completed.

While the pressure at the filter section 42 is lower than the pressure at the start of the ultrafiltration, the liquid transfer pump 50 operates. This allows the solution to be circulated in the closed loop formed by connecting the sample transfer tube $16_1$, $16_2$, $16_3$ thereby allowing the state of the solution to be more uniform.

(NMR Measurement)

Next, a magnetic field $B_0$ generated by the magnet $20_1$ and $20_2$ is applied to the sample solution containing a lock solvent to allow for a magnetic field lock. The magnetic field lock and the magnetic field $B_0$ generated by the magnet $20_1$ and $20_2$ are adjusted to obtain the uniformity thereof. Thus, the magnetic field $B_0$ required for the NMR measurement can be uniformly maintained.

After the magnetic field $B_0$ required for the NMR measurement is uniformly adjusted, the NMR measurement is repeatedly performed with operations for injecting and diluting small molecules. Accordingly, the NMR measurement can be performed while changing the concentration of small molecules in the sample solution.

(Control of Concentration of Small Molecules)

The sample solution is circulated by the liquid transfer pump 50 so as to form a flow of the sample solution in the closed loop formed by connecting the vessel 10, the sample transfer tubes $16_1$, $16_2$, $16_3$ and the filter section 42. The sample solution flows in the closed loop while a solution containing small molecules is placed into the solution injection unit 44 and controlled. Then, the solution containing the small molecules is injected into the closed loop. Pressure is applied to the injected small molecules by the liquid transfer pump 50, and the small molecules are transferred together with the sample solution through the sample tubing 16 to the vessel 10 which is equipped with the nuclear magnetic resonance probe 24. Unnecessary solutions produced during the injection of the small molecules are a buffer solution and a solution containing small molecules included in the sample solution before the injection of the solution containing the small molecules. The unnecessary solutions are discharged into the liquid reservoir 64 by the filter section 42. When the volume of the solutions discharged into the liquid reservoir 64 approaches to the volume of an injected solution, pressure indicated by the indicator 52 is reduced. Immediately after that, the liquid transfer pump 50 is stopped, and the pressure at the filter section 42 is reduced to a level lower than pressure required for the ultrafiltration performed by use of the filter section 42. Then, the ultrafiltration performed by using the filter section 42 is completed.

While the pressure at the filter section 42 is lower than the pressure at the start of the ultrafiltration, the solution is transferred. This allows the solution to be circulated in the closed loop formed by connecting the sample transfer tube $16_1$, $16_2$, $16_3$ thereby allowing the state of the solution to be more uniform.

During injection of small molecules, a solution containing small molecules or a buffer solution is discharged by the filter section 42. Thus, the concentration of large molecules in the closed loop is maintained to be constant while the concentration of small molecules is increased.

Repeatedly performing the injection of small molecules a plurality of times makes it possible to increase the concentration of small molecules in a sample solution used in the NMR measurement.

In the expressions shown below, the letter V indicates the entire volume of the closed loop formed by connecting the vessel 10 equipped with the probe and the sample transfer tubes $16_1$, $16_2$, $16_3$; $\alpha$, a concentration of small molecules present in the entire volume V before all injection operations are performed; $\beta$, a concentration of small molecules to be injected; and v, the volume of small molecules for one time of injection operation. In addition, E(i) indicates the amount of small molecules to be discharged by the filter section for the ith time of injection operation; M(i), the amount of small molecules remaining in the closed loop after the ith time of injection operation; and $\delta(i)$, the average concentration of small molecules remaining in the closed loop.

After the first injection operation, the amount E(1) of small molecules to be discharged, the amount M(1) of small molecules remaining in the closed loop, and the average concentration $\delta(1)$ of small molecules remaining in the closed loop, are expressed by expressions (1), (2), and (3).

$$E(1) = \alpha \times v \tag{1}$$

$$M(1) = \alpha \times (V - v) + \beta \times v \tag{2}$$

$$\delta(1) = \frac{M(1)}{V} \tag{3}$$

After an operation for injecting small molecules is repeated i times, the amount E(i) of small molecules to be discharged, the amount M(i) of small molecules remaining in the closed loop, and the average concentration $\delta(i)$ of small molecules remaining in the closed loop, are expressed by expressions (4), (5), and (6).

$$E(i) = \delta(i-1) \times v \tag{4}$$

$$M(i) = \delta(i-1) \times (V - v) + \beta \times v \tag{5}$$

$$\delta(i) = \frac{M(i)}{V} \tag{6}$$

(Dilution of Concentration of Small Molecules)

Similarly to the operation for injecting small molecules, an operation for diluting a concentration of small molecules is to inject a solvent not containing small molecules, such as a buffer solution, into the closed loop.

First, a sample solution is circulated in the closed loop by use of the liquid transfer pump 50. A flow of the sample solution is formed in the sample transfer tube $16_3$. A solution not containing small molecules whose amount is set by a measurer (or user) is injected from the solution injection unit 44. Pressure is applied to the injected solution by the liquid transfer pump 50 and transferred together with the sample solution through the sample transfer tube $16_2$ to the vessel 10 which is equipped with the nuclear magnetic resonance probe 24. Unnecessary solutions produced during the injection of the small molecules are discharged into the liquid reservoir 64 by the filter section 42 which discharges only a buffer solution and a solution containing small molecules present in the sample solution. Then, the operation of the liquid transfer pump 50 is stopped so as to reduce the pressure of the circulation of the flow in the closed loop to a level lower than the pressure required for the ultrafiltration. Accordingly, the ultrafiltration performed by using the filter section 42 is completed. As a result, the concentration of large molecules in the closed loop is maintained to be constant while the concentration of small molecules is reduced.

Repeating the operation for diluting a concentration of small molecules makes it possible to reduce a concentration of small molecules included in a sample solution used for the NMR measurement.

Next, in the expressions shown below, the letter V indicates the entire volume of the closed loop formed by connecting the vessel 10 equipped with the nuclear magnetic resonance probe 24 and the sample transfer tubes $16_1$, $16_2$, and the sample transfer tube $16_3$ provided in the control section 30; $\delta(0)$, a concentration of small molecules present in the volume V before dilution; v, the volume of a solution not containing small molecules for one time of the injection operation; E(i), the amount of small molecules to be discharged by the filter section in the ith time of the injection operation; M(i), the amount of small molecules remaining after the ith time of the injection operation; and $\delta(i)$, the average concentration of small molecules present in the closed loop.

After the first injection operation, the amount E(1) of small molecules to be discharged, the amount M(1) of small molecules remaining in the closed loop, and the average concentration $\delta(1)$ of small molecules remaining in the closed loop, are expressed by expressions (7), (8), and (9).

$$E(1) = \delta(0) \times v \quad (7)$$

$$M(1) = \delta(0) \times V - E(1) \quad (8)$$

$$\delta(1) = \frac{M(1)}{V} \quad (9)$$

After the operation for diluting the concentration of small molecules is repeated i times, the amount E(i) of small molecules to be discharged, the amount M(i) of small molecules remaining in the closed loop, and the average concentration $\delta(i)$ of small molecules remaining in the closed loop, are expressed by expressions (10), (11), and (12).

$$E(i) = \delta(i-1) \times v \quad (10)$$

$$M(i) = M(i-1) - E(i) \quad (11)$$

$$\delta(i) = \frac{M(i)}{V} \quad (12)$$

Combining the abovementioned operations makes it possible to increase or reduce the concentration of small molecules while maintaining the concentration of large molecules present in the sample solution to a constant level. In addition, after the NMR measurement is performed, the concentration of small molecules can be changed again. Furthermore, repeating the operations makes it possible to perform a series of the NMR measurement operations in which the concentration of small molecules is changed while maintaining large molecules to a constant amount and a constant concentration.

Figure 2:
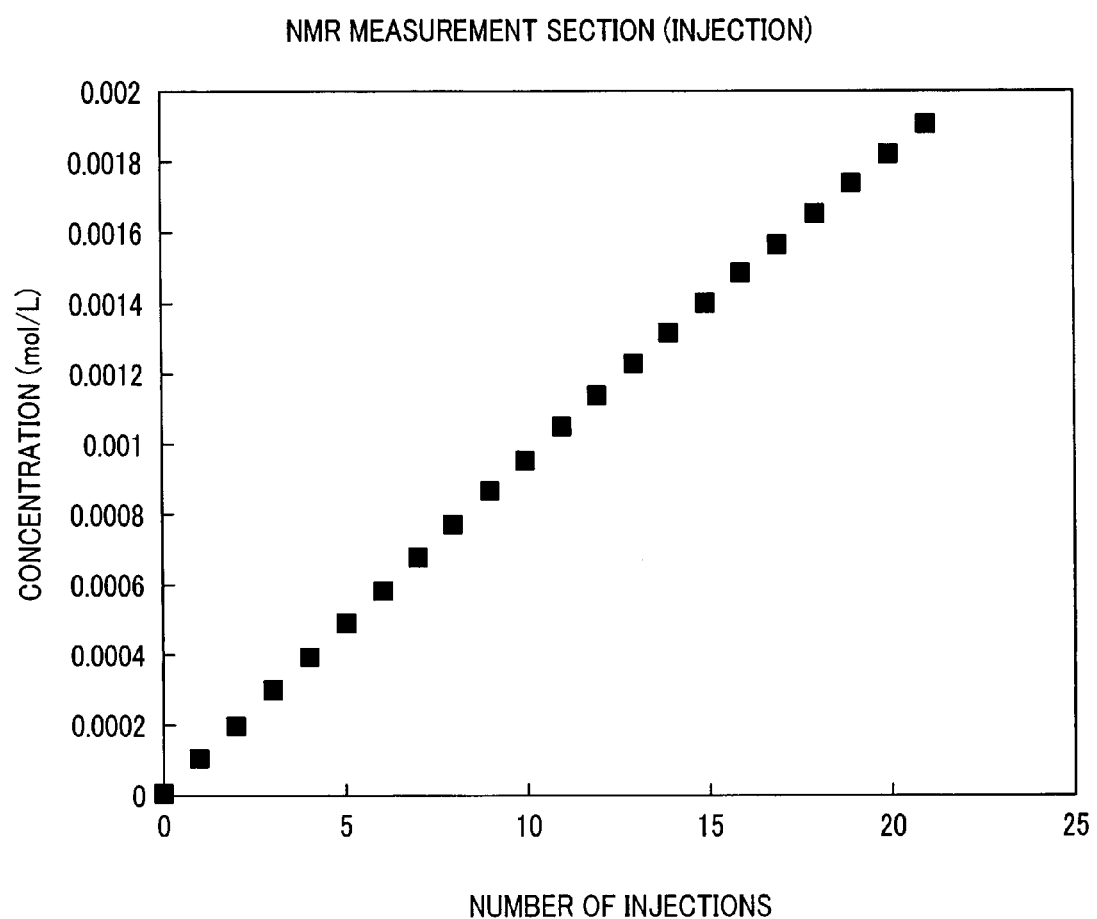
FIG. 2 is a graph showing an example of changes in concentration of small molecules in the case where the concentration of small molecules present in a closed loop is increased by an injection of a solution containing small molecules from a solution injection unit 44.
Figure 3:
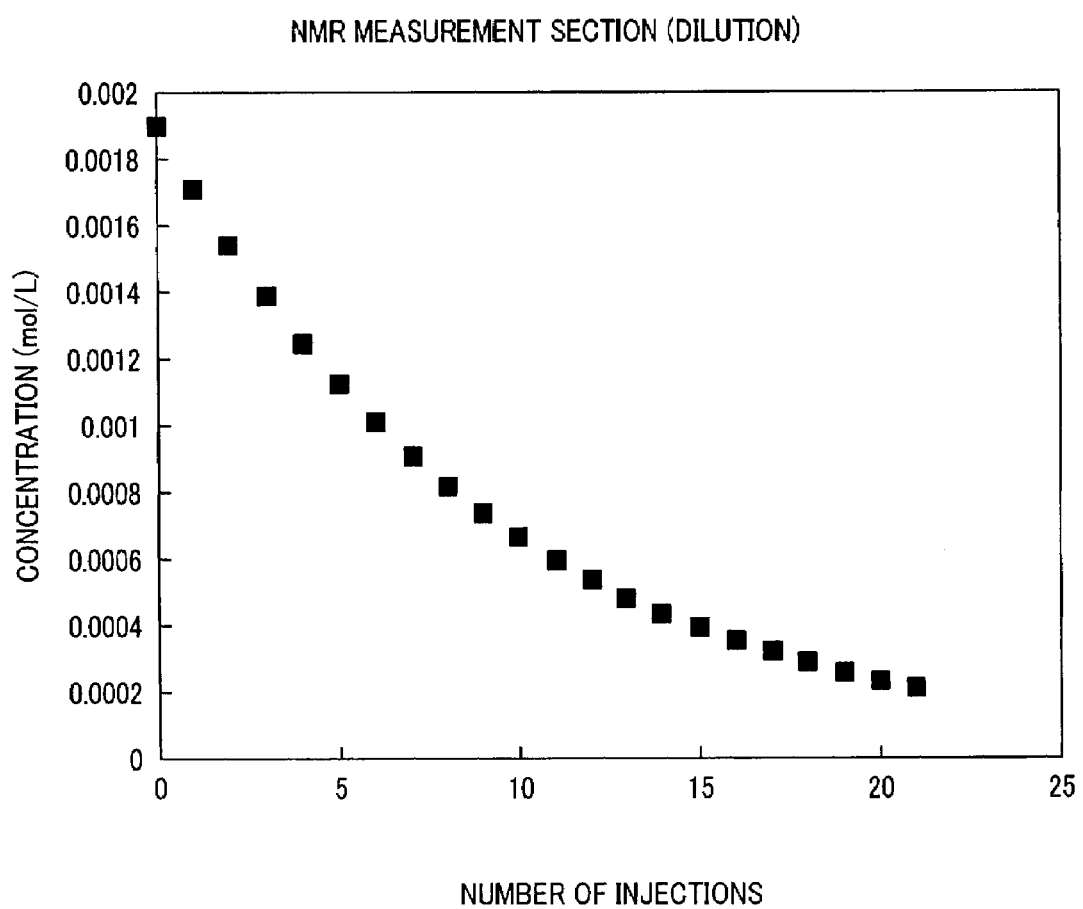
FIG. 3 is a graph showing an example of changes in concentration of small molecules in the case where the concentration of small molecules present in a closed loop is reduced by an injection of a solution not containing small molecules from a solution injection unit 44.

FIG. 2 is a graph showing an example of changes in the concentration of small molecules in the case where a solution containing small molecules is injected from the solution injection unit 44 so as to increase the concentration of small molecules present in the closed loop. FIG. 3 is a graph showing an example of changes in the concentration of small molecules in the case where a solution not containing small molecules is injected from the solution injection unit 44 so as to reduce the concentration of small molecules present in the closed loop.

In the graph shown in FIG. 2, the ordinate axis represents a concentration of small molecules present in the vessel 10 under the following conditions in which: the entire volume of the closed loop formed by connecting the vessel 10, the sample transfer tubes $16_1$, $16_2$, $16_3$ and the filter section 42 is 1000 μL; a concentration of small molecules before all injection operations are performed, 0 mol/L; a concentration of small molecules injected by all the injection operations, 0.01 mol/L; and the volume of a solution injected in one time of the injection operation from the solution injection unit 44, 10 μL. As the number of the injection operations is increased, the concentration of small molecules present in the vessel 10 is increased. Changes in the average concentration of small molecules due to injections of small molecules are expressed by expressions (1) to (6). In the example shown in FIG. 2, since the concentration of small molecules before all injection operations is 0 mol/L, the concentration α of small molecules present in the volume V before all injection operations is also 0 mol/L.

As described above, specifying a concentration of small molecules, the volume of small molecules to be injected in one time of the injection operation, and the number of the injection operations makes it possible to obtain a small molecule concentration that is set and to perform the NMR measurement under the abovementioned conditions.

In the graph shown in FIG. 3, the ordinate axis represents a concentration of small molecules present in the vessel 10 under the following conditions in which: the entire volume of the closed loop formed by connecting the vessel 10, the sample transfer tubes $16_1$, $16_2$, $16_3$ and the filter section 42 is 1000 μL; a concentration of small molecules before all injection operations are performed, 0.0019 mol/L; a concentration of small molecules injected by all the injection operations, 0.00 mol/L (i.e., only a buffer solution is injected); and the volume of a solution injected in one time of the injection operation from the solution injection unit 44, 100 μL. As the number of the injection operations is increased, the concentration of small molecules present in the vessel 10 is reduced. Changes in concentration of small molecules present in the vessel 10 based on the number of injection operations are expressed by expressions (10) to (12).

As mentioned above, specifying the volume of a solution not containing small molecules which is to be injected in one time of the injection operation, and the number of the injection operations makes it possible to obtain a small molecule concentration that is set and to perform the NMR measurement under the abovementioned conditions.

In addition, combining an operation for increasing the concentration of small molecules described above with an operation for decreasing the concentration of small molecules makes it possible to control an increase and reduction in the concentration of small molecules. Also, the combination of the above operations allows for reproduction of measurement conditions that have been once used for the NMR measurement and allows the NMR measurement to be performed under the reproduced measurement conditions.

When a lock solvent with a constant concentration is added to a solution containing or not containing small molecules which is to be injected into the closed loop, a concentration of the lock solvent present in the vessel 10 can be maintained to be constant during a series of injection operations.

(Replacement of Sample)

After a series of measurement operations on one sample is completed, the sample is replaced with another sample to perform the next measurement. In order to prevent contamination between samples, it is preferred that the following procedure be performed.

First, a sample containing large molecules remaining in the sample solution injection unit 46 and small molecules remaining in the solution injection unit 44 are removed. Next, the sample solution injection unit 46 and the solution injection unit 44 are washed with clean water, and clean water is poured into the units. Also, a solution(s) discharged in the liquid reservoir 64 are removed. Then, clean water is supplied through the liquid injection valve 48 while the liquid transfer pump 50 operates. Thus, the closed loop formed by connecting the sample transfer tubes $16_1$, $16_2$, $16_3$ is filled with the clean water. In this case, the clean water in the sample solution injection unit 46 and solution injection unit 44 is pressed out of the units so that connecting sections which connects the units with the sample transfer tube $16_3$ are washed. The clean water is circulated to some extent in the closed loop formed by connecting the sample transfer tubes $16_1$, $16_2$, $16_3$ by operating the liquid transfer pump 50. After that, clean water is supplied through the liquid injection valve 48 while the discharge valve 40 is opened. In the above state, the liquid transfer pump 50 continues to operate for a short time. After that, the liquid injection valve 48 and the discharge valve 40 are closed, and the operation of the liquid transfer pump 50 is stopped. As a result, the closed loop including the vessel 10 and the sample transfer tubes $16_1$, $16_2$, $16_3$ is filled with clean water. In this stage, a solution(s) discharged in the liquid reservoir 64 are removed. After that, the NMR measurement on another sample can be performed by first injecting a buffer solution. When the same buffer solution is used for the next measurement, the buffer solution may be used for washing instead of clean water. In this case, the procedure for injecting a buffer solution can be eliminated.

Preferable connections between the vessel 10 and the sample transfer tube $16_1$ and between the vessel 10 and the sample transfer tube $16_2$ are described below.

Figure 4A:
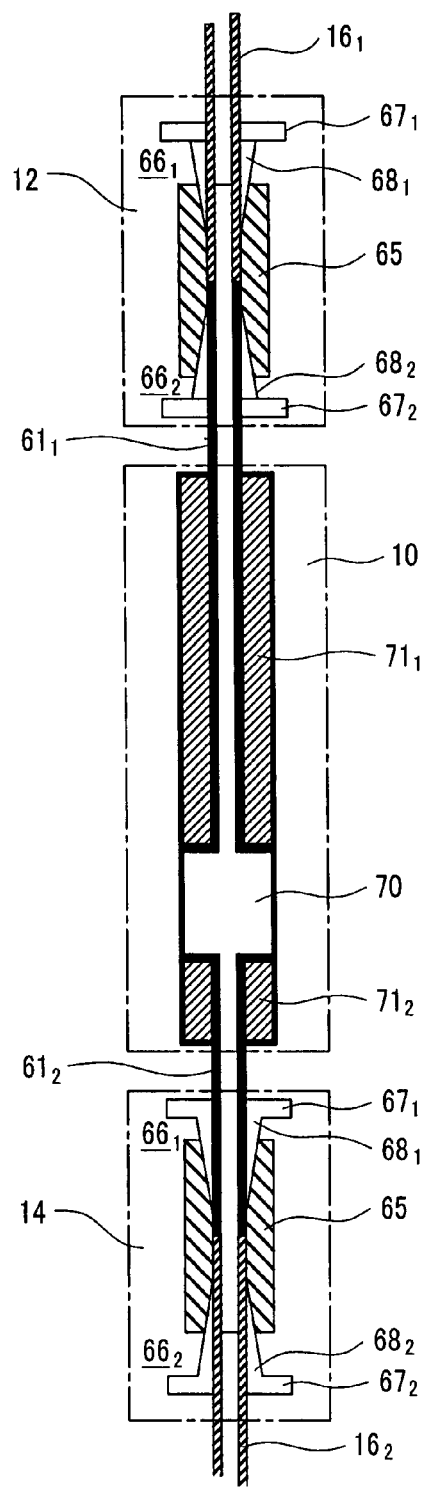
FIGS. 4A and 4B are diagrams showing two examples of connections of a vessel 10 with sample transfer tubes $16_1$ and $16_2$.
Figure 4B:
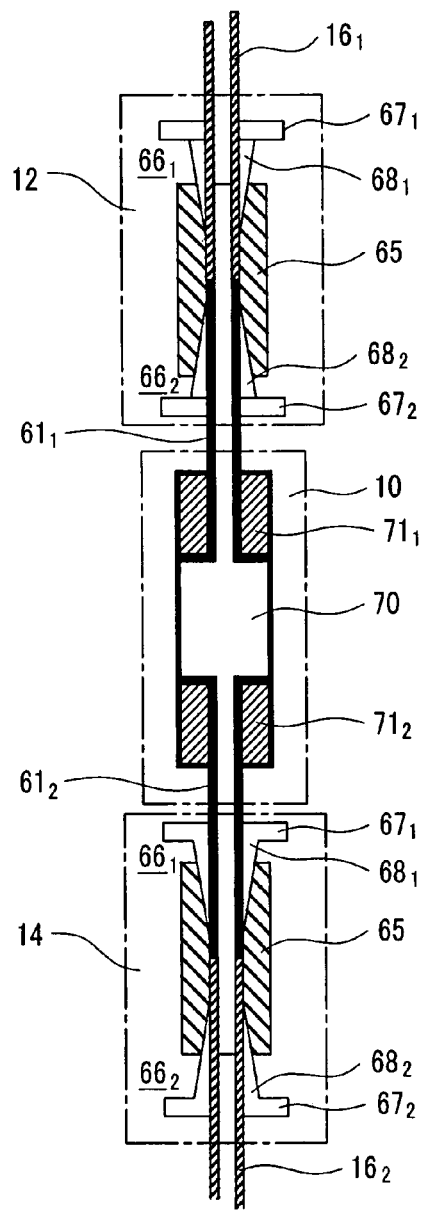

FIGS. 4A and 4B are diagrams showing two examples of a connection structure in which connection tubes $61_1$ and $61_2$ connecting the vessel 10 with the sample transfer tube $16_1$ $16_2$, respectively, each protrude from both end portions of the vessel 10. In both examples, the vessel 10 includes an NMR measurement section 70 and guide sections $71_1$, $71_2$ each having a wall thickness. The structure of the vessel 10 including those sections may be easily formed of, for example, glass in an integrated manner. In FIG. 4A, the guide section $71_1$ is made longer than the guide section $71_2$, whereas in FIG. 4B, the length of the guide section $71_1$ is substantially equal to that of the guide section $71_2$. For a configuration in which the nuclear magnetic resonance probe 24 supports the vessel 10, the structure shown in FIG. 4A is suitable, whereas for a configuration in which the nuclear magnetic resonance probe 24 supports the vessel 10 and the sample tube connection sections 12, 14, the structure shown in FIG. 4B is suitable.

It is preferred that the connection tubes $61_1$ and $61_2$ have the same outer diameter as that of the sample transfer tubes $16_1$ and $16_2$. The preferred outer diameter ranges from 1.57 mm to 0.36 mm. The inner diameters of the connection tubes $61_1$, $61_2$ and those of the guide sections $71_1$, $71_2$ preferably range from 0.5 mm to 0.065 mm. It is necessary that a sufficient amount of a sample for the NMR measurement be stored in the NMR measurement section. Thus, when proteins are used as large molecules, the volume of the NMR measurement section 70 preferably ranges from 400 μL to 100 μL. The NMR measurement section 70 is designed to have an inner diameter sufficient to place a sample in an area of a magnetic field that is generated by the separated magnets $20_1$ and $20_2$ and that is suitable for the NMR measurement.

The sample tube connection sections 12 and 14 each have a connector 65 and set screws $66_1$ and $66_2$, which are compression type connectors used for HPLC. There are two types of the set screws $66_1$ and $66_2$: an integrated type and a separated type in which nuts $67_1$ and $67_2$ are separated from ferrets $68_1$ and $68_2$. Both types are suitable for the connection structure used in the sample tube connection sections 12 and 14. The connector 65 and the set screws 661, $66_2$ are preferably made of PEEK, PTEF, Kel-F, Tefzel, or another material which is known in a HPLC field. The connection tubes $61_1$ and $61_2$ are each inserted into the connector 65 and the guide sections $71_1$ and $71_2$, respectively, and fixed by the set screws $66_1$ and $66_2$. In addition, the nuts $67_1$ and $67_2$ are provided to serve as loose fasteners for the connections.

FIGS. 5A and 5B are diagrams showing two examples of a connection structure in which the sample transfer tubes $16_1$ and $16_2$ are inserted from both end portions of the vessel 10 into narrow tubes provided in the guide sections $71_1$ and $71_2$ each having a wall thickness, the guide sections $71_1$ and $71_2$ being disposed in the vessel 10. In the examples, the lengths of the guide sections $71_1$ and $71_2$ may be selected based on the structure of the nuclear magnetic resonance probe 24. When proteins are used as large molecules which are a sample, the NMR measurement section 70 preferably ranges from 400 μL to 100 μL. The NMR measurement section 70 is designed to have an inner diameter sufficient to place a sample in an area of a magnetic field that is generated by the separated magnets $20_1$ and $20_2$ and that is suitable for the NMR measurement. It is preferred that the inner diameter of the narrow tubes of the guide sections $71_1$ and $71_2$ be equal to the outer diameter of the sample transfer tubes $16_1$ and $16_2$ connected with the guide sections $71_1$ and $71_2$, respectively. The preferred inner diameter of the narrow tubes ranges from 1.57 mm to 0.36 mm. Reference numerals $69_1$ and $69_2$ are shrink tubes. After the sample transfer tubes $16_1$ and $16_2$ are inserted into the guide sections $71_1$ and $71_2$, the shrink tubes $69_1$ and $69_2$ are used to compress and fix the connections between them. For the shrink tubes $69_1$ and $69_2$, a tube, which is made of Teflon (a registered trademark), Tefzel or another material known in a HPLC field and has heat shrink properties, is preferably used.

Second Embodiment

Figure 6:
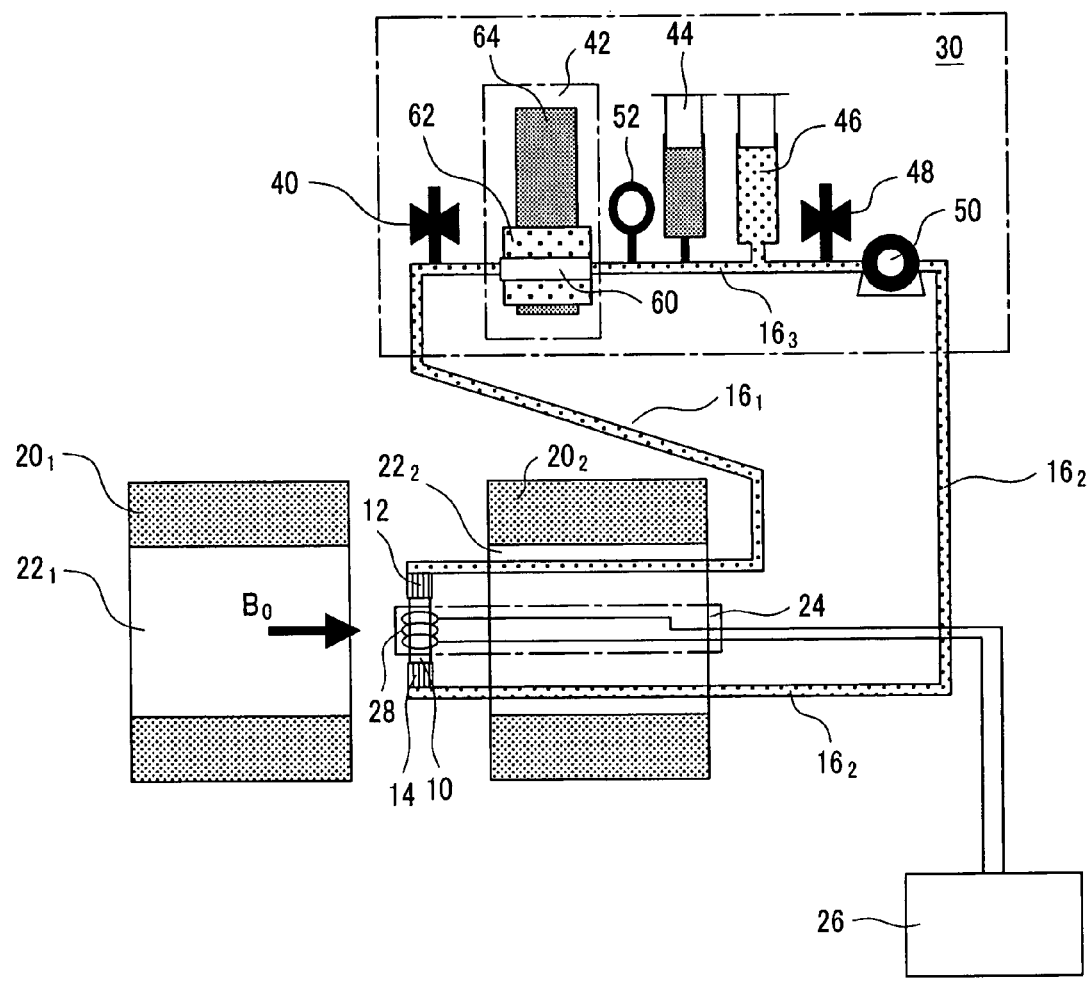
FIG. 6 is a schematic diagram showing a circulated flow nuclear magnetic resonance measurement apparatus according to a second embodiment of the present invention.

FIG. 6 is a schematic diagram showing the configuration of a circulated flow nuclear magnetic resonance measurement apparatus according to a second embodiment of the present invention. In FIG. 6, the same constituent elements as those in the first embodiment shown in FIG. 1 are denoted by the same reference numerals. As seen upon comparing FIG. 1 with FIG. 6, the configuration according to the second embodiment is substantially the same as the configuration according to the first embodiment except that the sample transfer tubes $16_1$ and $16_2$ connected with the vessel 10 through the sample tube connection sections 12 and 14, respectively, are bent at connection portions of the sample transfer tubes $16_1$ and $16_2$ and pass through a bore $22_2$. A measurement procedure in the second embodiment may be the same as that in the first embodiment.

According to the second embodiment, when the outer diameters of the separated magnets $20_1$ and $20_2$, which are used to apply a magnetic field to a sample, are large, there is an advantage in that the total length of the sample transfer tubes $16_1$ and $16_2$ can be reduced. In the second embodiment, the structures shown in FIGS. 4B and 5B are desirably used for the vessel 10.

Third Embodiment

Figure 7:
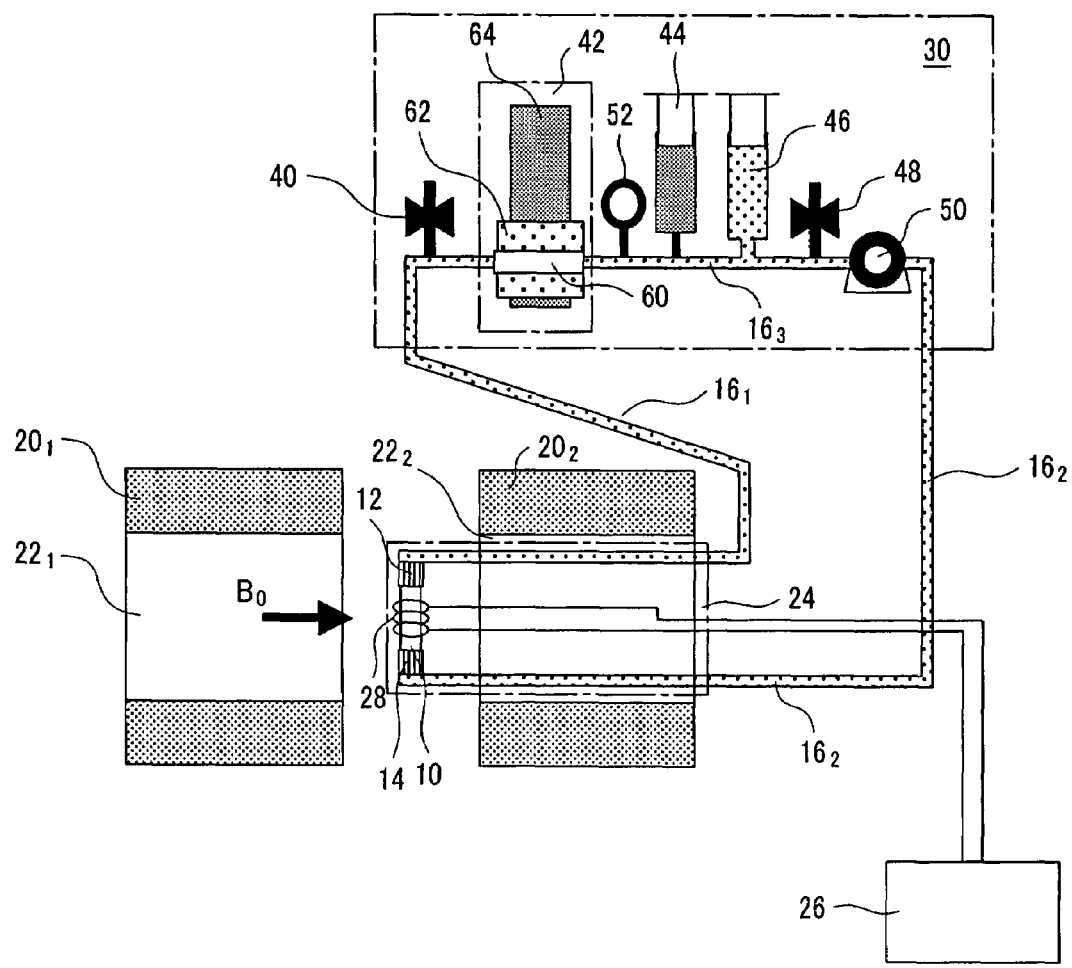
FIG. 7 is a schematic diagram showing a circulated flow nuclear magnetic resonance measurement apparatus according to a third embodiment of the present invention.

FIG. 7 is a diagram showing the configuration of a circulated flow nuclear magnetic resonance measurement apparatus according to a third embodiment of the present invention. In FIG. 7, the same constituent elements as those in the second embodiment shown in FIG. 6 are denoted by the same reference numerals. As seen upon comparing FIG. 6 with FIG. 7, the configuration according to the third embodiment is substantially the same as the configuration according to the second embodiment except that the nuclear magnetic resonance probe 24 is configured to include the vessel 10, the sample tube connection sections 12, 14, and parts in the vicinity of the connection portions of the sample transfer tubes $16_1$ and $16_2$ connected with the vessel 10 through the sample tube connection portions 12 and 14, respectively. A measurement procedure in the third embodiment may be the same as that in the second embodiment.

According to the third embodiment, when the outer diameters of the separated magnets $20_1$ and $20_2$, which are used to apply a magnetic field to a sample, are large, there is an advantage in that the total length of the sample transfer tubes $16_1$ and $16_2$ can be reduced. In addition, the vessel 10 can be firmly supported by the nuclear magnetic resonance probe 24.

Fourth Embodiment

Figure 8:
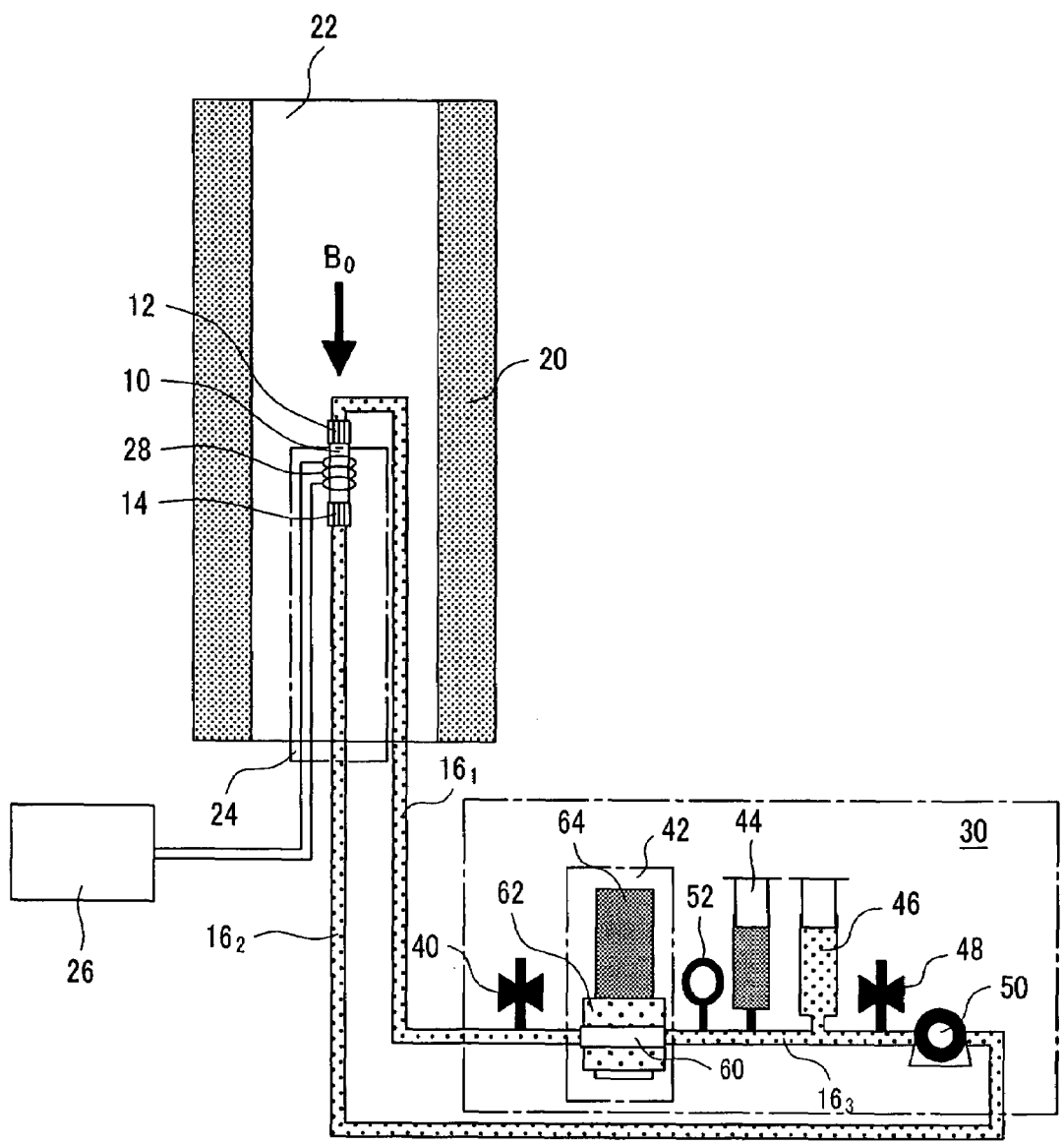
FIG. 8 is a schematic diagram showing a circulated flow nuclear magnetic resonance measurement apparatus according to a fourth embodiment of the present invention.

FIG. 8 is a diagram showing the configuration of a circulated flow nuclear magnetic resonance measurement apparatus according to a fourth embodiment of the present invention. In FIG. 8, the same constituent elements as those in the first embodiment shown in FIG. 1 are denoted by the same reference numerals. As seen upon comparing FIG. 1 with FIG. 8, the configuration according to the fourth embodiment is substantially the same as the configuration according to the first embodiment except that the nuclear magnetic resonance probe 24 including the vessel 10 is provided in the bore 22 of a separated magnet 20 used to apply a magnetic field to a sample, and that a magnetic field $B_0$ is directed parallel to the longitudinal direction of the vessel 10. A measurement procedure in the fourth embodiment may be the same as that in the first embodiment.

According to the fourth embodiment, when the separated magnet 20 of a small size, which is used to apply a magnetic field to a sample, is used, there is an advantage in that the total length of the sample transfer tubes $16_1$ and $16_2$ can be reduced.

Fifth Embodiment

Figure 9:
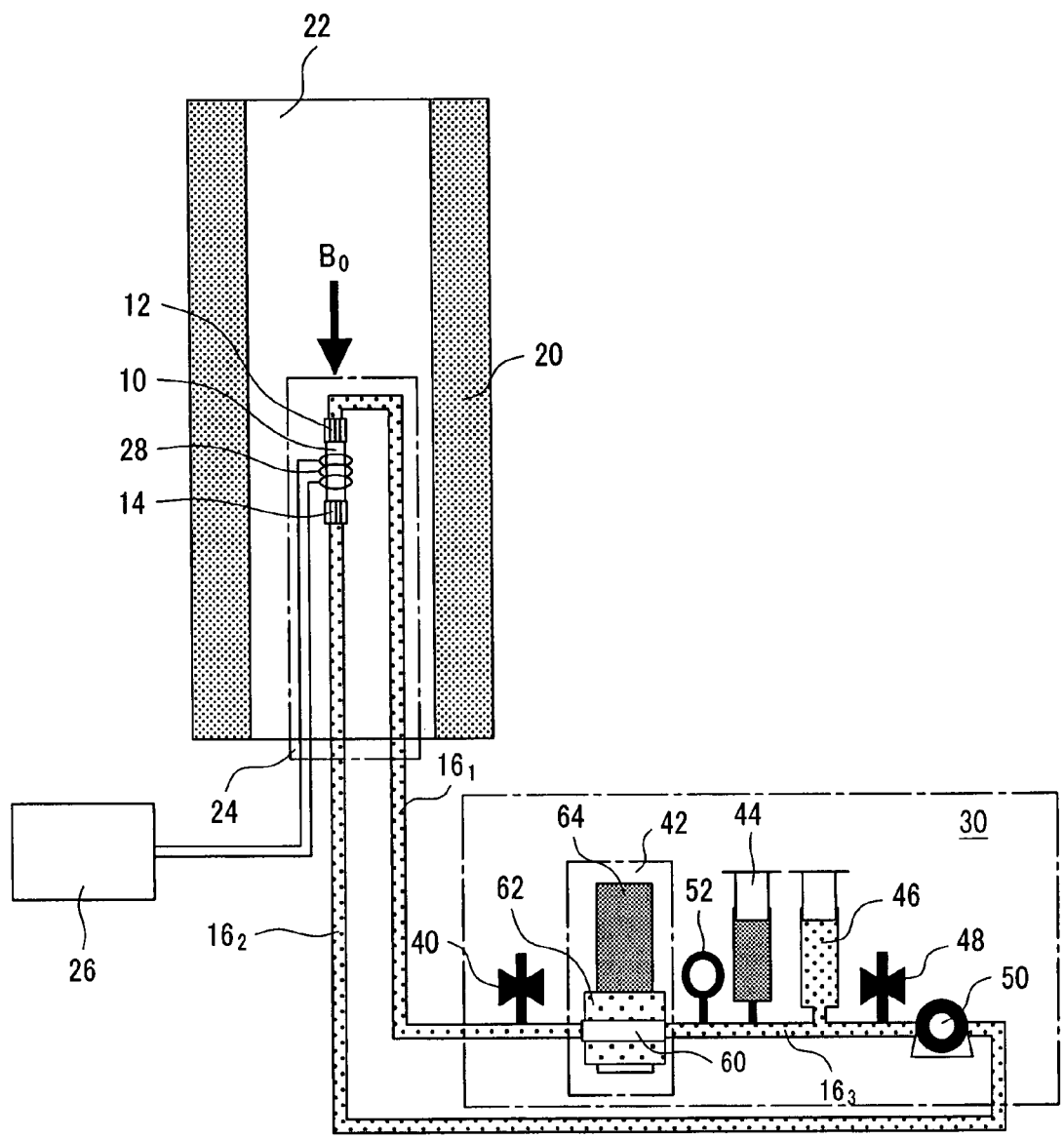
FIG. 9 is a schematic diagram showing a circulated flow nuclear magnetic resonance measurement apparatus according to a fifth embodiment of the present invention.

FIG. 9 is a diagram showing the configuration of a circulated flow nuclear magnetic resonance measurement apparatus according to a fifth embodiment of the present invention. In FIG. 9, the same constituent elements as those in the fourth embodiment shown in FIG. 8 are denoted by the same reference numerals. As seen upon comparing FIG. 8 with FIG. 9, the configuration according to the fifth embodiment is substantially the same as the configuration according to the fourth embodiment except that the nuclear magnetic resonance probe 24 is configured to include the vessel 10, the sample tube connection sections 12, 14, and parts in the vicinity of the connection portions of the sample transfer tubes $16_1$ and $16_2$ connected with the vessel 10 through the sample tube connection portions 12 and 14, respectively. A measurement procedure in the fifth embodiment may be the same as that in the fourth embodiment.

According to the fifth embodiment, the vessel 10 can be firmly supported by the nuclear magnetic resonance probe 24.

Sixth Embodiment

Figure 10:
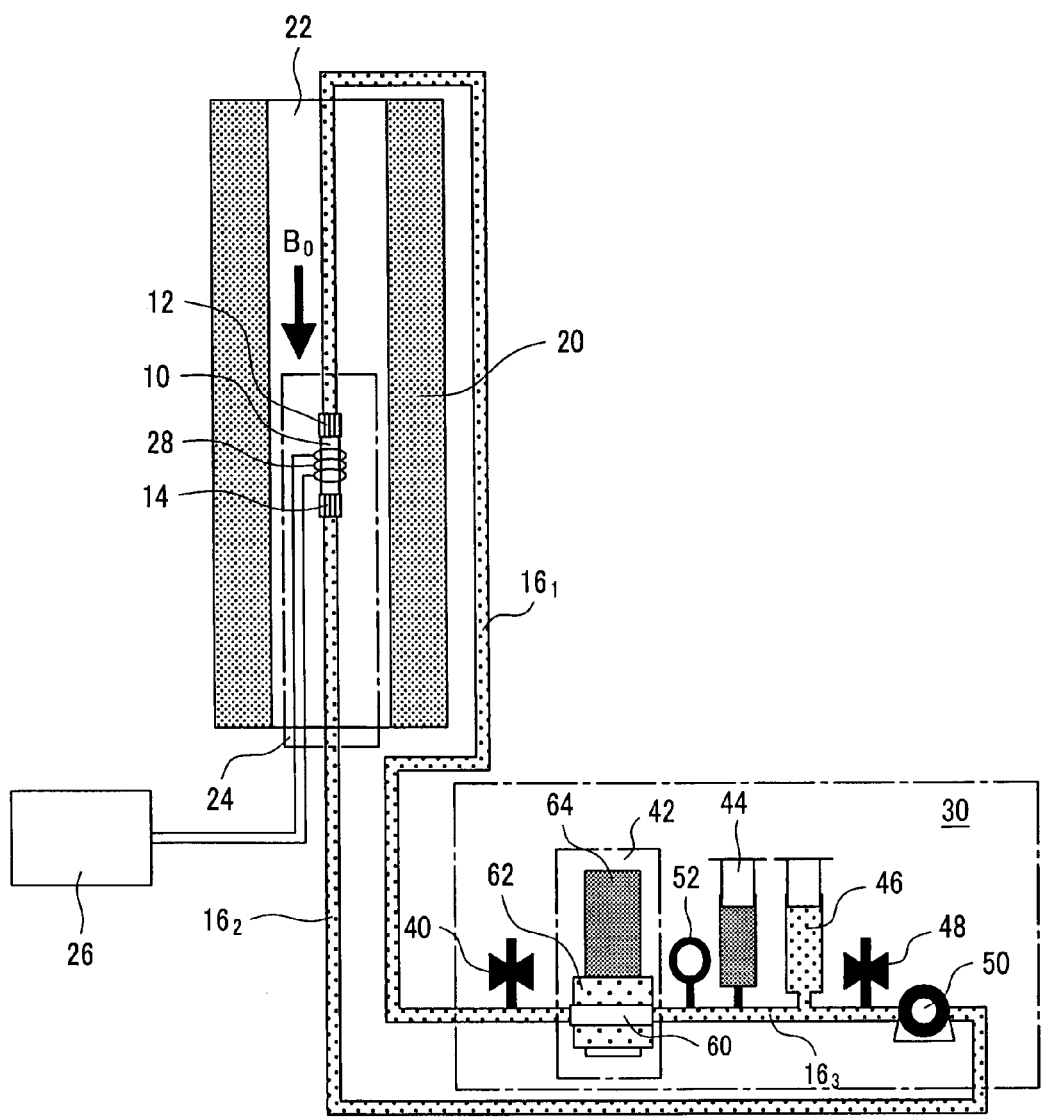
FIG. 10 is a schematic diagram showing a circulated flow nuclear magnetic resonance measurement apparatus according to a sixth embodiment of the present invention.

FIG. 10 is a diagram showing the configuration of a circulated flow nuclear magnetic resonance measurement apparatus according to a sixth embodiment of the present invention. In FIG. 10, the same constituent elements as those in the fifth embodiment shown in FIG. 9 are denoted by the same reference numerals. As seen upon comparing FIG. 9 with FIG. 10, the configuration according to the sixth embodiment is substantially the same as the configuration according to the fifth embodiment except that the nuclear magnetic resonance probe 24 is configured to include the vessel 10, the sample tube connection sections 12, 14, and parts in the vicinity of the connection portions of the sample transfer tubes $16_1$ and $16_2$ connected with the vessel 10 through the sample tube connection portions 12 and 14, respectively, and that a part of the sample transfer tube $16_1$, the vessel 10, and a part of the sample transfer tube $16_2$ are arranged along a straight line. A measurement procedure in the sixth embodiment may be the same as that in the fifth embodiment.

According to the sixth embodiment, the inner diameter of the bore 22 of the magnet 20, which is used to apply a magnetic field to a sample, can be reduced (compared with the structure of the fifth embodiment), which makes it possible to reduce the size of the entire apparatus.

Seventh Embodiment

Figure 11:
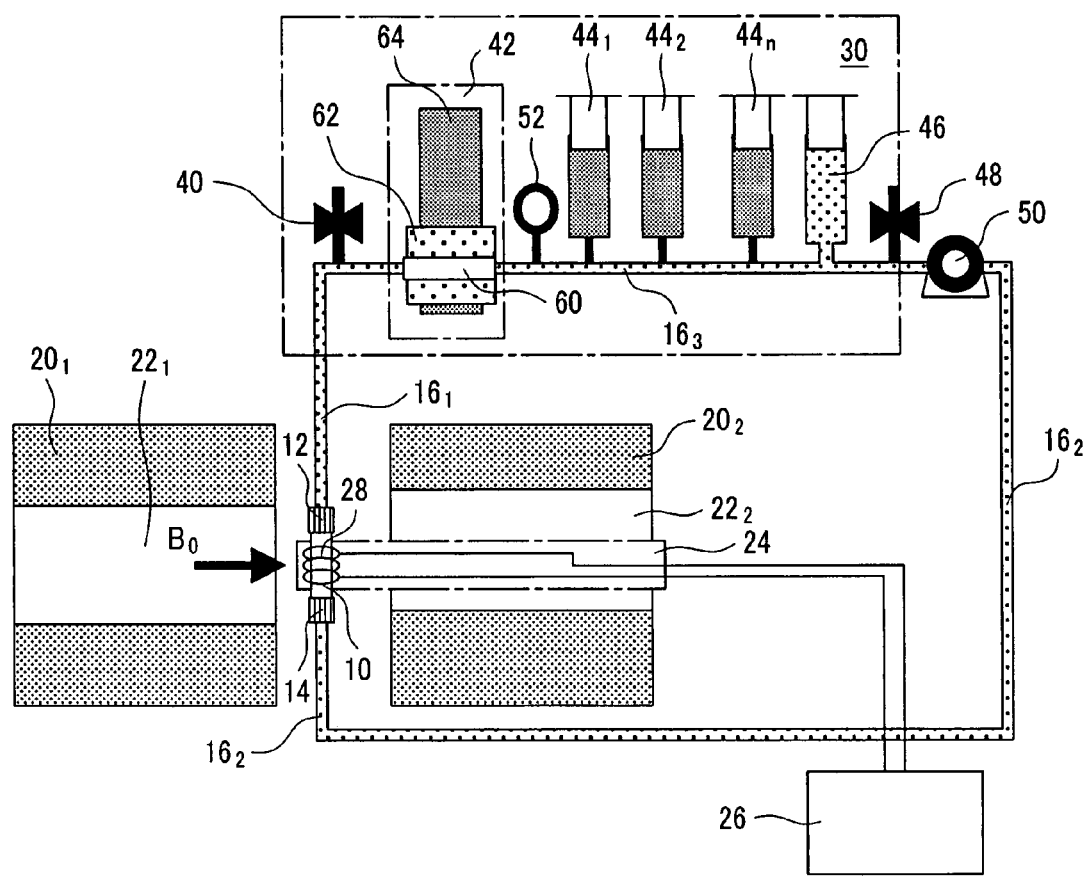
FIG. 11 is a schematic diagram showing a circulated flow nuclear magnetic resonance measurement apparatus according to a seventh embodiment of the present invention.

FIG. 11 is a diagram showing a configuration of a circulated flow nuclear magnetic resonance measurement apparatus according to a seventh embodiment of the present invention. In FIG. 11, the same constituent elements as those in the first embodiment shown in FIG. 1 are denoted by the same reference numerals. As seen upon comparing FIG. 1 with FIG. 11, the configuration according to the seventh embodiment is substantially the same as the configuration according to the first embodiment except that an N number of the solution injection units 44 ($44_1$, $44_2$, ... $44_n$) are arranged. Specifically, according to the seventh embodiment, solutions each containing a different type of small molecules are injected from independent syringes of the solution injection units 44 for measurement on a single sample. Accordingly, the seventh embodiment provides a method in which, while maintaining a concentration of large molecules to be measured in the vessel 10 to a constant level and maintaining a concentration of a certain type of small molecules to a constant level, concentrations of the other types of small molecules can be adjusted.

A procedure for the measurement in the seventh embodiment may be similar to that in the first embodiment. A description will be made of a preferred method for maintaining a concentration of small molecules to a constant level while increasing concentrations of other types of small molecules.

(a) A sample solution containing large molecules which are a sample is injected into the closed loop formed by connecting the vessel 10, the sample transfer tubes $16_1$, $16_2$, and the sample transfer tube $16_3$ provided in the control section 30.

(b) A concentration of small molecules to be injected to maintain a concentration of small molecules present in the vessel 10 to a constant level is set to a value β. A solution containing the small molecules to be injected is set in a syringe of the solution injection unit $44_1$.

(c) Solutions each containing a different type of small molecules, which is different from the type of small molecules that are set in the process (b), are set in the solution injection units $44_2, \ldots 44_n$. The total volume of the solutions each containing a different type of the small molecules to be injected is a value Vex.

(d) The volume v of the solution containing the small molecules (to be injected) which is set in the process (b) to maintain a concentration α of small molecules present in the vessel 10 to a constant level is set to satisfy expression (13).

$$v = \frac{\alpha}{\beta - \alpha} V_{ex} \qquad (13)$$

(e) The solution containing the small molecules set in the process (b) and the solutions each containing a different type of small molecules set in the process (c) are injected into the sample solution that has been injected in the process (a). In this case, as described in the first embodiment, an unnecessary solution(s) are discharged into the liquid reservoir 64 of the filter section 42.

A description will be made of a preferred method for maintaining a concentration of small molecules to a constant level while diluting concentrations of other types of small molecules.

(f) A sample solution containing large molecules is injected into the closed loop formed by connecting the vessel 10, the sample transfer tubes $16_1$, $16_2$, and the sample transfer tube $16_3$ provided in the control section 30.

(g) A concentration of small molecules to be injected to maintain a concentration of small molecules present in the vessel 10 to a constant level is set to a value β. A solution containing the small molecules to be injected is set in a syringe of the solution injection unit $44_1$.

(h) A solution not containing small molecules is set in syringes of the solution injection units $44_2, \ldots 44_n$. In this case, the total volume of the solution not containing small molecules is a value Vex.

(i) The volume v of the solution containing the small molecules which is set in the process (g) to maintain a concentration α of small molecules present in the vessel 10 is set to satisfy expression (13).

(j) The solution containing the small molecules set in the process (g) and the solution not containing small molecules set in the process (h) are injected into the sample solution that has been injected in the process (f). In this case, as described in the first embodiment, an unnecessary solution(s) are discharged into the liquid reservoir 64 of the filter section 42.

The configuration in which an N number of the solution injection units 44 ($44_1, 44_2, \ldots 44_n$) are arranged may be applied to the configurations according to the second to sixth embodiments in a similar manner to the seventh embodiment.

Furthermore, in the configuration according to the seventh embodiment, the NMR measurement can be performed while each small molecule concentration in a solution containing a plurality of types of small molecules is independently changed by combining the following operations: the operation for injecting small molecules; the operation for diluting small molecules; the operation for maintaining a concentration of a certain type of small molecules to a constant level while increasing concentrations of other types of small molecules; and the operation for maintaining a concentration of a certain type of small molecules to a constant level while diluting concentrations of other types of small molecules.

Applying the present invention to large molecules (e.g., proteins) having functional properties in a living body allows the NMR measurement to be repeated in which solution conditions are changed while maintaining a large molecules to a constant amount and maintaining the volume of a sample to be constant irrespective of titration conditions. In the life science field, the abovementioned NMR measurement improves the efficiency of analysis of biochemical processes in a living organism. Furthermore, in the medical and drug discovery fields, the NMR measurement is expected to be used to improve efficiencies of analysis of and screening of disease mechanisms by performing a measurement on binding affinity with disease related proteins.

What is claimed is:

1. An apparatus for performing a nuclear magnetic resonance measurement, the apparatus comprising:
   a magnet for applying a magnetic field to a sample;
   a nuclear magnetic resonance probe that is arranged in an area in which a magnetic field is generated by the magnet;
   a vessel that is equipped with the nuclear magnetic resonance probe and stores the sample;
   a transmitting/receiving system for transmitting an electromagnetic wave to the sample present in the vessel or receiving an electromagnetic wave from the nuclear magnetic resonance probe;
   sample tubing that forms a closed loop including the vessel; and
   a control section provided with a part of the sample tubing;
   wherein the control section includes:
   means for injecting a solution containing large molecules to be measured into the sample tubing;
   means for injecting a solution containing small molecules into the sample tubing;
   a liquid transfer pump for circularly transferring a solution present in the vessel and the sample tubing, which form the closed loop;
   a filter that allows the small molecules to be selectively discharged when pressure in the sample tubing is increased to a predetermined level or more by an operation of the liquid transfer pump; and
   means for monitoring the pressure in the sample tubing.

2. The apparatus for performing a nuclear magnetic resonance measurement according to claim 1, wherein
   the control section further includes means for injecting a buffer solution or clean water into the sample tubing and a discharge valve for discharging a solution present in the vessel and the sample tubing, which form the closed loop.

3. The apparatus for performing a nuclear magnetic resonance measurement according to claim 1, wherein
   the filter is connected to the sample tubing through a film or a hollow material which discharges only small molecules or a liquid included in the sample to the outside of the closed loop in response to an increase in pressure in the sample tubing; and
   the filter is provided with a liquid reservoir for storing small molecules or a liquid that passes through the film or the hollow material.

4. The apparatus for performing a nuclear magnetic resonance measurement according to claim 1, wherein
   the means for injecting a solution containing large molecules and the means for injecting a solution containing small molecules each include a syringe pump, and the amount of a solution to be injected from each of the syringe pumps is controlled by an electronics device.

5. The apparatus for performing a nuclear magnetic resonance measurement according to claim 1, wherein
the liquid transfer pump is adapted to transfer a solution under constant pressure in the vessel and the sample tubing, which form the closed loop, by use of a plunger driven by an electronically controllable stepping motor.

6. The apparatus for performing a nuclear magnetic resonance measurement according to claim 1, wherein
the means for injecting a solution containing small molecules into the sample tubing is adapted to inject a solution not containing small molecules, instead of a solution containing small molecules.

7. The apparatus for performing a nuclear magnetic resonance measurement according to claim 1, wherein
a plurality of the means for injecting a solution containing small molecules into the sample tubing are disposed; and
the types of small molecules placed in each of the means for injecting a solution containing small molecules are different from each other.

8. The apparatus for performing a nuclear magnetic resonance measurement according to claim 7, wherein
at least one of the plurality of means for injecting a solution containing small molecules into the sample tubing is adapted to inject a solution not containing small molecules.

9. A method for a nuclear magnetic resonance measurement, the method using an apparatus that is adapted to perform the nuclear magnetic resonance measurement and that includes:
a magnet for applying a magnetic field to a sample;
a nuclear magnetic resonance probe that is arranged in an area in which a magnetic field is generated by the magnet;
a vessel that is equipped with the nuclear magnetic resonance probe and stores the sample;
a transmitting/receiving system for transmitting an electromagnetic wave to the sample present in the vessel or receiving an electromagnetic wave from the nuclear magnetic resonance probe;
sample tubing that forms a closed loop including the vessel; and
a control section provided with a part of the sample tubing;
wherein the control section includes:
means for injecting a solution containing large molecules to be measured into the sample tubing;
means for injecting a solution containing small molecules into the sample tubing;
a liquid transfer pump for circularly transferring a solution present in the vessel and the sample tubing, which form the closed loop;
a filter that allows the small molecules to be selectively discharged when pressure in the sample tubing is increased to a predetermined level or more by an operation of the liquid transfer pump;
means for monitoring the pressure in the sample tubing;
means for injecting a buffer solution or clean water into the sample tubing; and
a discharge valve for discharging a solution present in the vessel and the sample tubing, which form the closed loop,
the method for the nuclear magnetic resonance measurement comprising the steps of:
supplying a buffer solution to the sample tubing through the means for injecting a buffer solution or clean water into the sample tubing while operating the liquid transfer pump so as to fill the vessel and the sample tubing with the buffer solution, the vessel and the sample tubing forming the closed loop;
subsequently injecting a sample solution containing large molecules to be measured into the vessel and the sample tubing which form the closed loop by using the means for injecting large molecules while operating the liquid transfer pump; and
subsequently injecting a sample solution containing small molecules into the vessel and the sample tubing which form the closed loop by using the means for injecting small molecules while operating the liquid transfer pump;
wherein a relative amount of the small molecules with respect to the large molecules is changed while maintaining the amount of the large molecules present in the vessel and the sample tubing to a predetermined value, the vessel and the sample tubing forming the closed loop.

10. The method for the nuclear magnetic resonance measurement according to claim 9, wherein
an operation for injecting a sample solution containing small molecules into the vessel and the sample tubing which form the closed loop, or an operation for injecting a sample solution not containing small molecules into the vessel and the sample tubing instead of injecting a solution containing small molecules, is repeatedly performed if required.

* * * * *